US011992405B2

(12) United States Patent
Hou et al.

(10) Patent No.: US 11,992,405 B2
(45) Date of Patent: May 28, 2024

(54) PERCUTANEOUS SLING FOR PAPILLARY MUSCLE APPROXIMATION

(71) Applicant: Boston Scientific Scimed, Inc., Maple Grove, MN (US)

(72) Inventors: Dongming Hou, Plymouth, MN (US); Raffaele Cicerone, Galway (IE); Bryan A. Clark, Forest Lake, MN (US); Aiden Flanagan, Galway (IE); Tim O'Connor, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 287 days.

(21) Appl. No.: 17/108,191

(22) Filed: Dec. 1, 2020

(65) Prior Publication Data

US 2021/0161667 A1    Jun. 3, 2021

Related U.S. Application Data

(60) Provisional application No. 62/942,779, filed on Dec. 3, 2019.

(51) Int. Cl.
*A61F 2/24*     (2006.01)
*A61B 17/00*    (2006.01)
*A61B 17/04*    (2006.01)

(52) U.S. Cl.
CPC ........ *A61F 2/2457* (2013.01); *A61B 17/0469* (2013.01); *A61F 2/2466* (2013.01); *A61B 2017/00853* (2013.01)

(58) Field of Classification Search
CPC .................. A61F 2/2457; A61F 2/2466; A61F 2220/0016; A61F 2250/001;
(Continued)

(56) References Cited

U.S. PATENT DOCUMENTS 10,058,428 B1    8/2018    Neustadter
10,271,950 B2    4/2019    Neustadter
(Continued)

OTHER PUBLICATIONS

International Search Report and Written Opinion for the International Patent Application No. PCT/US2020/062652, dated Jun. 1, 2021, 19 pages.
(Continued)

*Primary Examiner* — Sarah A Long
*Assistant Examiner* — Raihan R Khandker
(74) *Attorney, Agent, or Firm* — Seager, Tufte & Wickhem, LLP

(57) ABSTRACT

An implant system and method of delivery includes a catheter system including a sling catheter having a plurality of distal openings and a delivery catheter, disposed within the sling catheter and having a distal port. Suture coupled anchors may be sequentially delivered by the delivery catheter to a cardiac treatment site by aligning the port of the delivery catheter with different openings of the sling catheter and pushing the anchor through the port and the sling catheter to embed the anchor into cardiac tissue such as tissue of a papillary muscle. Each anchor may have a linear configuration for translation within the delivery catheter and a biased configuration that inhibits its reentry into the sling catheter once deployed. Once all anchors are deployed, the suture may be tightened, the anchored portion of the sling catheter may be detached, and the catheter system withdrawn.

20 Claims, 10 Drawing Sheets

(58) Field of Classification Search
CPC ...... A61B 17/0469; A61B 2017/00853; A61B 2017/0409; A61B 2017/0414; A61B 2017/0443; A61B 2017/0464; A61B 2017/003; A61B 2017/0437
See application file for complete search history.

(56) References Cited

U.S. PATENT DOCUMENTS

| | | |
|---|---|---|
| 10,517,729 B2 | 12/2019 | Neustadter |
| 10,548,732 B2 | 2/2020 | Neustadter |
| 2006/0190030 A1* | 8/2006 | To .................... A61B 17/068 606/205 |
| 2007/0027533 A1 | 2/2007 | Douk |
| 2010/0217283 A1 | 8/2010 | St. Goar et al. |
| 2010/0280604 A1 | 11/2010 | Zipory et al. |
| 2013/0226290 A1* | 8/2013 | Yellin .................... A61F 2/2448 623/2.11 |

OTHER PUBLICATIONS

Ancora Heart—https://www.ancoraheart.com/—retrieved Jul. 31, 2019—6 pages.
Edwards Cardioband™ Mitral Reconstruction System—Edwards Lifesciences Corporation—2018.
Edwards Cardioband™ Mitral Reconstruction System—Introduction and overview—Two-year follow up of CE Tria—Edwards Lifesciences Corporation—2018.
Hvass, U, et al., Papillary Muscle Sling: A New Functional . . . , Ann. Thorac Surg 2003, 75:809-11.
Hvass, U, et al.,The Papillary Muscle Sling for Ischemic Mitral RegurgitationThe Journal of Thoracic and Cardiovascular Surgery c vol. 139, No. 2.

* cited by examiner

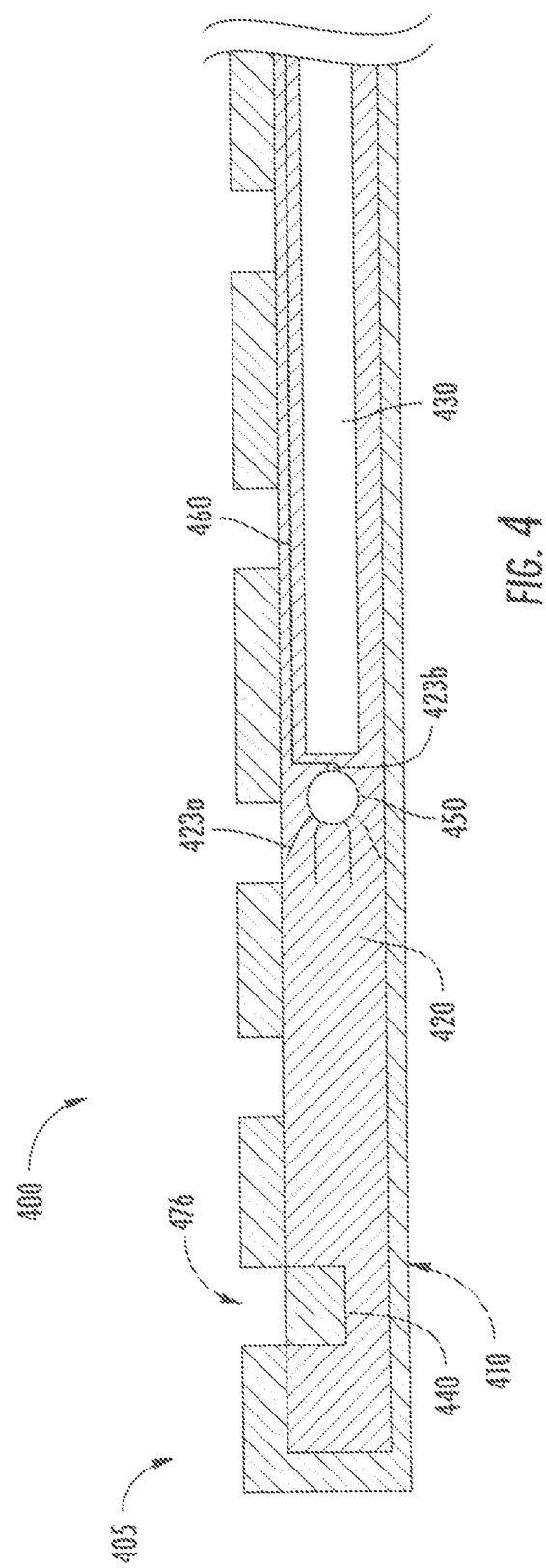

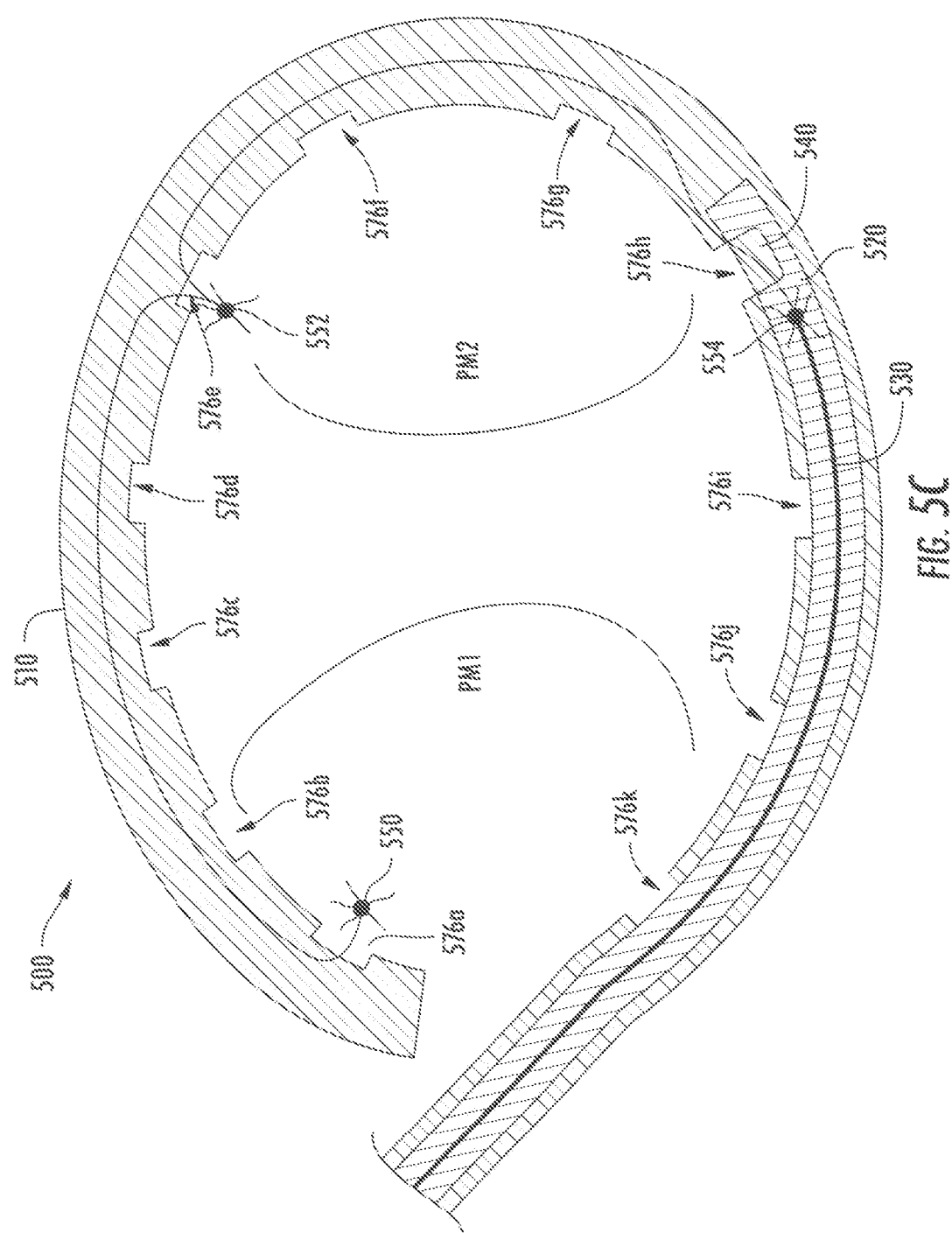

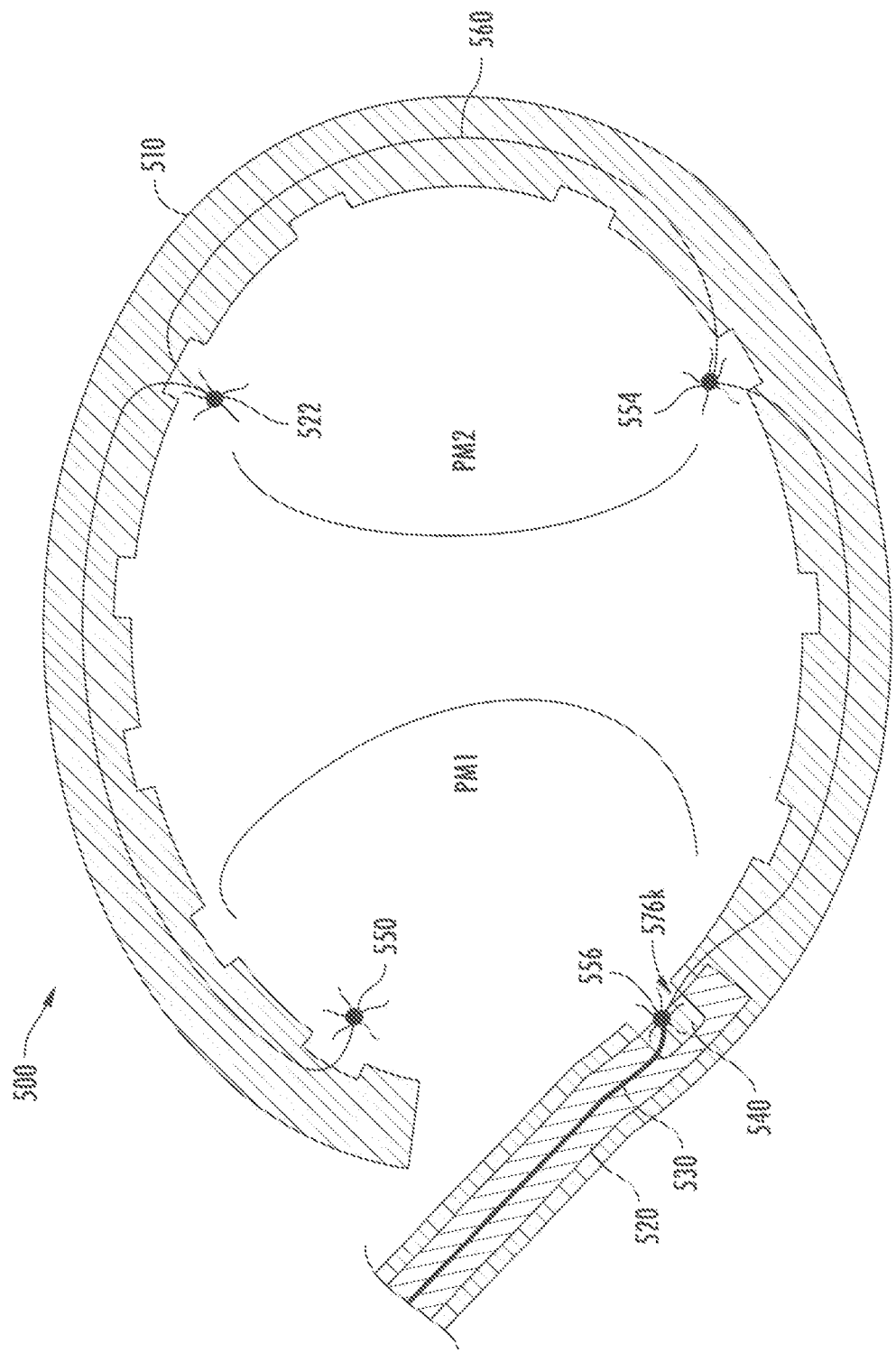

INSIDE DELIVERY CATHETER PROFILE

DEPLOYED PROFILE

PERCUTANEOUS SLING FOR PAPILLARY MUSCLE APPROXIMATION

CROSS-REFERENCE TO RELATED APPLICATIONS

The present application claims the benefit of priority under 35 U.S.C. § 119 to U.S. Provisional Patent Application 62/942,779, filed Dec. 3, 2019, which application is incorporated herein by reference in its entirety for all purposes.

FIELD

The present disclosure relates generally to the field of implantable medical devices and more particularly to implantable devices, systems, and methods for adjusting heart features.

BACKGROUND

Mitral insufficiency (MI) is a form of heart disease where the mitral annulus excessively dilates and the valve leaflets no longer effectively coapt during systolic contraction. Regurgitation occurs during ventricular contraction and cardiac output decreases.

An annuloplasty procedure may be performed to restore the physiological form and function of the mitral annulus. Annuloplasty procedures may involve surgically implanting a ring around the mitral annulus to restore a diameter of the patient's mitral annulus to that of a healthy state where the valve leaflets properly coapt and mitral regurgitate flow is minimized. Additionally, sub-valvular repair procedures such as repositioning of papillary muscles or repairing chordae within the left ventricle may be performed.

Due to the invasive nature of the surgical approaches to mitral valve repair, several transcatheter techniques have been developed to emulate surgical approaches. Because delivery catheters that carry mitral valve or sub-valvular components may extend up to 52" in length, it can be challenging to accurately transport and deliver components to a treatment site.

SUMMARY

One general aspect includes an implant including a sling catheter having a first opening and a second opening, the first opening and second opening extending through a wall of the sling catheter, a first anchor configured to be disposed adjacent and external to the first opening of the sling catheter, a second anchor configured to be disposed adjacent and external to the second opening of the sling catheter and a suture, extending through a lumen of the sling catheter, the suture having a first end coupled to the first anchor, and a second end coupled to the second anchor.

In various embodiments, the first opening and the second opening are two of a plurality of spaced apart openings of the sling catheter, where the spaced apart openings may be evenly spaced or variably spaced. The sling catheter may be comprised of a polytetrafluoroethylene tube. At least one of the first opening or the second opening may be oriented towards a papillary muscle. The first opening and the second opening may be aligned along a common longitudinal axis of the sling catheter or disposed along different longitudinal axes of the sling catheter. The first anchor and the second anchor may be two of a plurality of anchors of the implant, and each anchor may be biased towards a configuration that inhibits return of the anchor into the sling catheter.

According to another aspect, a delivery system includes a first catheter having a proximal end, a distal end and a lumen extending from the proximal end to the distal end, where a portion of the distal end of the first catheter includes a sling having a plurality of spaced apart openings extending through a first catheter wall. The system may include a second catheter having a proximal end, a distal end, and a delivery lumen extending from the proximal end to the distal end, the distal end of the second catheter including a delivery port that extends through a second catheter wall. The second catheter may be translatably disposed within the lumen of the first catheter to enable alignment of the port with one or more of the plurality of spaced apart openings of the sling. The delivery system may also include a plurality of anchors and a push tube, translatably disposed within the delivery lumen and configured to advance at least one of the plurality of anchors through the delivery lumen and through the delivery port.

In various embodiments, the sling of the first catheter may be formed of a polytetrafluoroethylene tube. The sling may have a higher flexibility than the second catheter. The outer diameter of the sling may be between 1 millimeters (mm) and 12 mm, may have a length of the sling between 1 centimeter (cm) to 35 cm and the plurality of spaced apart openings may be spaced at least 2 mm apart. In some embodiments, the plurality of anchors may be coupled via one or more sutures. In some embodiments, a cinch mechanism may be configured to reduce spacing between the plurality of anchors, where in some embodiments the cinch mechanism may be configured to detach the sling from the first catheter. The cinch mechanism may be configured to bind at least a portion of the suture to at least one anchor.

In some embodiments, each of the plurality of anchors may comprise a first configuration enabling translation through the second catheter and delivery port, and a second configuration that inhibits translation through the delivery port, and the second catheter may retain the plurality of anchors in the second configuration. In some embodiments, the plurality of spaced apart openings of the sling may be aligned along a common longitudinal axis of the first catheter or may be disposed along different longitudinal axes of the first catheter. The plurality of spaced apart openings may be evenly spaced or a spacing of plurality of spaced apart openings may vary. For example, spacing of openings in regions expected to be contacting papillary muscles may be closer, enabling adequate flexibility in number and position of anchors placed. The delivery system may include a cinching mechanism for tightening the sutures.

According to another aspect, a method of sub valvular repair includes advancing a catheter system to a left ventricle, the catheter system including a sling catheter having a plurality of openings extending through a distal wall of the sling catheter and a delivery catheter, translatably disposed within the sling catheter, the delivery catheter having a distal port extending through a wall of the delivery catheter. The method includes orienting the plurality of openings towards papillary muscles and advancing a first anchor towards the distal port of the delivery catheter, the first anchor having a linear configuration enabling translation of the first anchor through the delivery catheter. The method includes aligning the distal port with a first opening of the sling catheter and pushing the first anchor through the distal port and the first opening into first papillary tissue, the first anchor assuming a biased configuration that inhibits return of the first anchor into the first opening when the first anchor is pushed from the delivery catheter and advancing a second anchor towards the distal port of the delivery catheter, the second anchor having the linear configuration during translation through the delivery catheter, the second anchor may be coupled to the first anchor by a suture. The method includes aligning the distal port with a second opening of the sling catheter. The method includes pushing the second anchor through the distal port and the second opening into second papillary tissue, the second anchor assuming the biased configuration that inhibits return of the second anchor into the second opening when the second anchor is pushed from the delivery catheter and tightening the suture to draw the first anchor and the second anchor together to adjust a spacing between the first papillary tissue and the second papillary tissue.

In some embodiments, the method may further include: binding one or more portions of the suture to at least one anchor, detaching at least a portion of the sling catheter, and removing the catheter system from the left ventricle.

With such an arrangement, an implant and method of delivery is disclosed which enables non-invasive sub-valvular repair.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical illustrated component is typically represented by a single numeral. For purposes of clarity, not every component is labeled in every figure, nor is every component of each embodiment shown where illustration is not necessary to allow those of ordinary skill in the art to understand the disclosure. In the figures:

FIG. 4 is a cross-sectional view of a distal end of the sling catheter, anchor catheter, and push tube as disclosed herein in one embodiment;

FIGS. 5A-5E illustrate examples of steps that may be performed to deploy anchors to papillary tissue for sub-valvular repair using one embodiment of the delivery system disclosed herein.

DETAILED DESCRIPTION

An implant system and method of delivery includes a catheter system including a sling catheter having a plurality of distal openings and an anchor delivery catheter, disposed within the sling catheter and having a distal port. Suture coupled anchors may be sequentially delivered by the anchor delivery catheter to a cardiac treatment site by aligning the port of the anchor delivery catheter with different openings of the sling catheter and pushing the anchor through the port and the sling catheter to embed the anchor into cardiac tissue such as tissue of a papillary muscle. Each anchor may have a linear configuration for translation within the delivery catheter and a biased configuration that inhibits its reentry into the sling catheter once deployed. Once all anchors are deployed, the suture may be tightened, the anchored portion of the sling catheter may be detached, and the catheter system withdrawn. Such a system may be used to bring tissue features of the heart closer together, for example, for valvular and/or sub-valvular repair procedures such as annuloplasty and repair, replacement and/or repositioning of a valve leaflet, a papillary muscle, or chordae to improve valve function.

These and other beneficial aspects of a system for sub-valvular repair are described in more detail below. It should be noted that, although embodiments of the present disclosure may be described with specific reference to papillary muscles, the principles disclosed herein may be readily adapted to benefit any other dilatation, valve incompetency, valve leakage, and other similar heart failure conditions.

As used herein, the term "distal" refers to the end farthest away from the medical professional when introducing a medical device into a patient, while the term "proximal" refers to the end closest to the medical professional when introducing a medical device into a patient.

Figure 1:
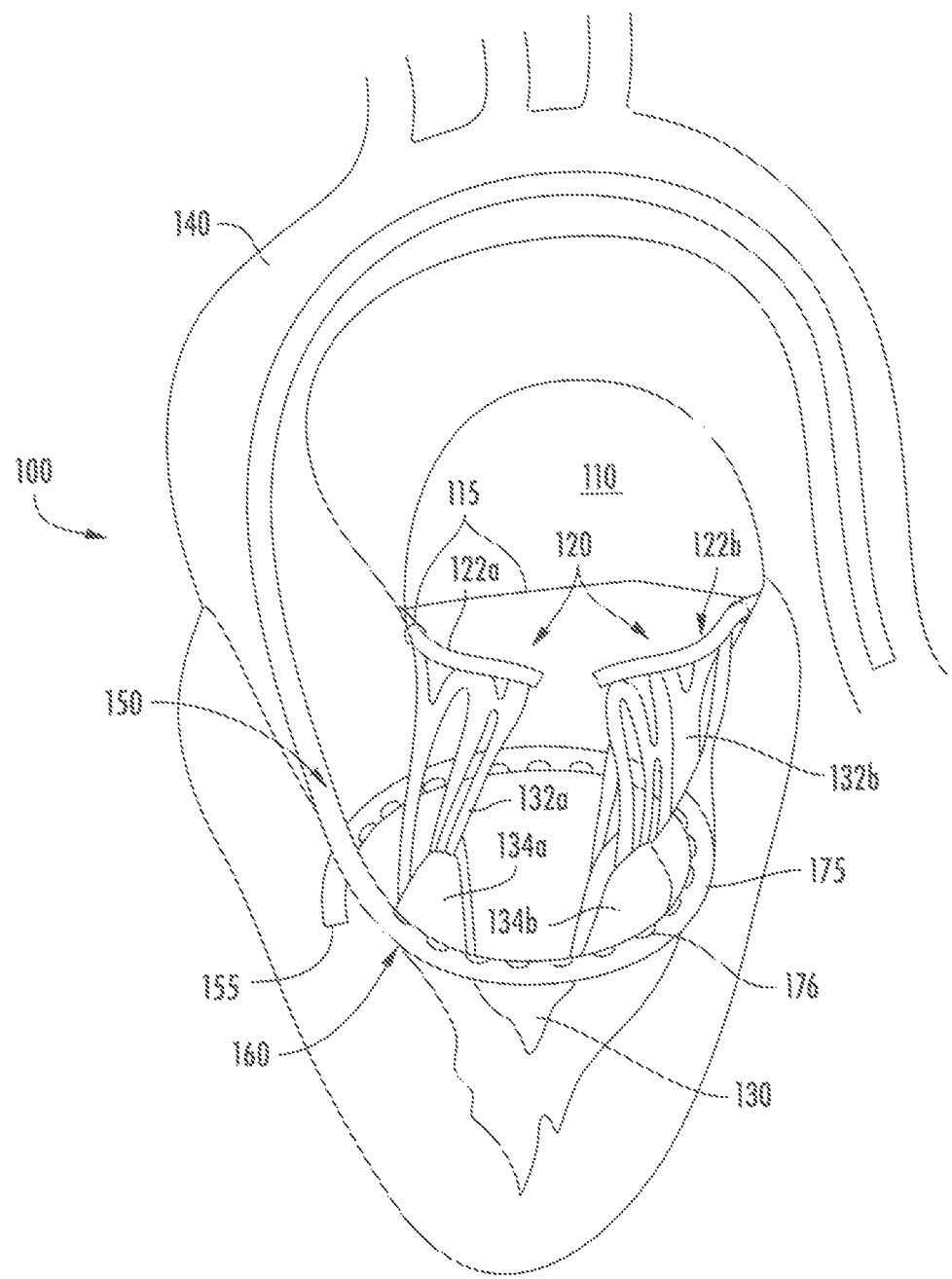
FIG. 1 is a diagram of a portion of a heart in which delivery catheters such as those disclosed in various embodiments herein may be deployed.

FIG. 1 is a diagram of a left chamber of a heart 100, including a left atrium 110 separated from a left ventricle 130 by a mitral valve 120. The mitral valve 120 includes an anterior leaflet 122a and a posterior leaflet 122b which are attached in a healthy heart to respective papillary muscles 134a, 134b via chordae tendineae 132a, 132b. The papillary muscles 134a, 134b contract to prevent inversion or prolapse of the leaflets 122a, 122b on contraction of the left ventricle 130. A mitral annulus 115 comprises a fibrous ring that, in a healthy heart is saddle shaped and of a diameter to enable the valves to close, or coapt, during systolic contraction.

In a diseased heart, one or more of the chordae tendineae 132a, 132b may be stretched or ruptured, resulting in a flailing leaflet 122a, 122b that no longer effectively closes, resulting in regurgitation. Alternatively, or in conjunction, the mitral annulus 115 may become stretched or deformed, and the valves may also fail to close as a result.

To repair the heart failure condition, repair components may be transluminally deployed to the heart 100. In FIG. 1, a delivery system 150 as disclosed herein is shown advanced through a femoral artery to the aorta 140 and into the left ventricle 130 for transfemoral retrograde delivery of repair components. Depending upon the heart feature that is to be repaired it is appreciated that the present disclosure is not limited by the manner in which the delivery system is introduced to the heart 100. For example, to deliver repair components to a left atrium, a transapical or transseptal delivery pathway may be used with embodiments of the delivery catheter and system disclosed herein.

In one embodiment, the delivery system 150 may include a plurality of nested catheters having a steerable distal end 155 to facilitate navigation of repair components into the left ventricle. According to one aspect, as described in more detail below, the delivery system 150 includes a sling catheter 160 including a detachable distal portion comprising a tubular sling 175 having a plurality of openings 176 extending therethrough.

During delivery, a distal guidewire (not shown) disposed within the sling catheter 160 may assist with transluminal navigation. For example, as shown in FIG. 1, the distal guidewire may deliver the sling 175 into the left ventricle 130, pushing the sheath against the wall of the left ventricle around the base of the papillary muscles 134a, 134b. An anchor delivery catheter translatably disposed within the sling 175 may advance one or more suture coupled anchors through openings 176 of the sling 175 into papillary tissue. Following anchor deployment, the suture may be cinched to draw together the papillary muscles, to approximate a healthy papillary structure where leaflets 122a, 122b are drawn together to improve cardiac function. As will be now described in more detail below, the sling 175 may then be detached and remain within the left ventricle to retain the papillary muscles in their restructured state.

Figure 2A:
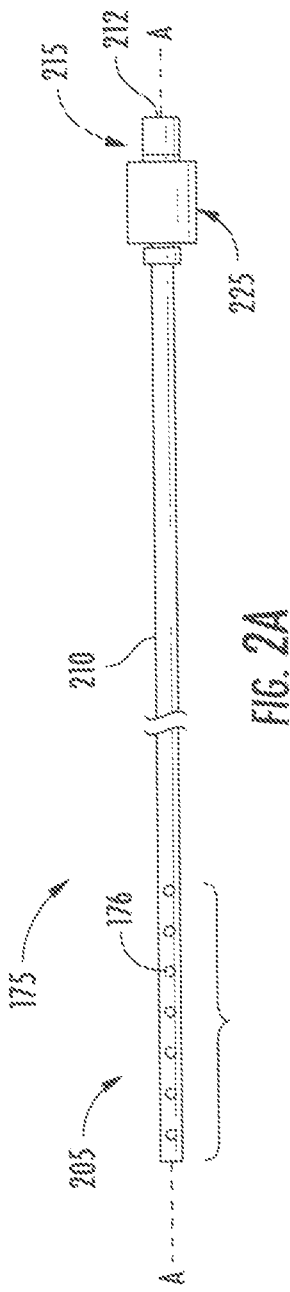
FIGS. 2A and 2B illustrate several embodiments of a sling catheter in accordance with the present disclosure.
Figure 2B:
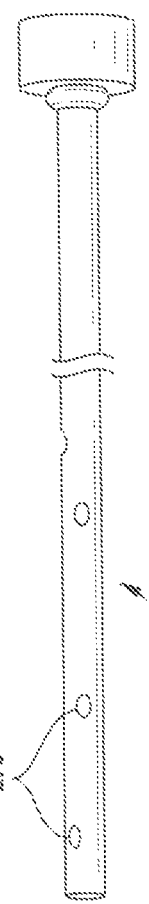
Figure 3:
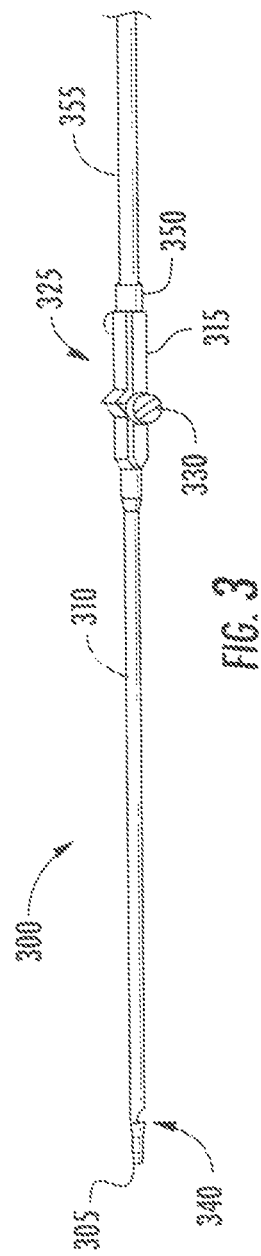
FIG. 3 illustrates one embodiment of an anchor delivery catheter in accordance with various aspects of the present disclosure.

FIGS. 2A, 2B and 3 illustrate examples of catheters that may form the nested catheters of the delivery system 150 (FIG. 1). For example, FIG. 2A illustrates a top down perspective view of one embodiment of the sling catheter 160. In some embodiments, the sling catheter 160 may include a tubular body having a proximal end 215, a distal end 205, and an elongate body 210 extending therebetween. A lumen 212 may extend from the proximal end through the distal end of the sling catheter 160 along axis 'A' in FIG. 2A. A connector 225 may be disposed at the proximal end 215, enabling the sling catheter 160 to be releasably coupled to a connector of a steerable catheter that may be used to guide the sling catheter 160 into position within the cardiac cavity. The connector 225 may take any of a variety of forms, for example including but not limited to a screw connector, a snap fit connector, a Luer connector, etc. Accordingly, the disclosure is not limited to the mechanism for coupling the sling catheter 160 to a steerable catheter.

In one embodiment, the sling catheter 160 is formed of a pliant material such as a polytetrafluoroethylene (PTFE) tube or other various materials suitable for implantable devices. The sling catheter 160 may comprise varying properties and/or materials along the length of the sling 175 or around the cross-sectional diameter of the sling 175 to achieve the properties desired (e.g., abrasion resistance, strength, etc.). The sling catheter 160 may comprise a composite material, such as fibers of one material embedded into a matrix of a second material. Some examples of materials (in addition to those already noted) may include polyether-polyurethane (PE-PUR copolymers), poly(styrene-isobutylene-styrene) (SIBS) tri-block polymers, polyisobutylene urethane copolymers (PIB-PUR), polyisobutylene (PIB), polyethylene or other similar materials. In some embodiments, the length of the sling catheter 160 may range from between 24"-52", and more particularly between 42"-46". In one embodiment, the inner diameter of the sling catheter 160 may range between 0.75 mm-11.5 mm, and the outer diameter may range between 1 mm-12 mm or more. In an example of an embodiment, an inner diameter may be, for example 28Fr and the outer diameter may be 32Fr.

As described, in some embodiments a distal end 205 of the sling catheter 160 includes a plurality of openings 176. According to one aspect, the distal portion 205 of the sling catheter 160 that includes the plurality of openings 176 is referred to as a 'sling'. The length of the sling may range from between 1 and 35 cm. For example, longer slings are envisioned which may wrap circumferentially multiple times around the papillary muscles (2-3 or more) within the left ventricle. In some embodiments, the plurality of openings include spaced apart openings having a cross section diameter selected to enable an anchor to pass through the opening into cardiac tissue. For example, the cross-sectional diameter of openings may range between 0.50 mm and 10 mm. In some embodiments, the openings 176 are evenly spaced apart. In alternate embodiments, the spacing between openings may vary, for example, to provide closer openings at areas of the sling that may be positioned adjacent to papillary muscles and may have increased spacing over areas of the sling that may be generally disposed between papillary muscles. In some embodiments, the plurality of spaced apart openings may be aligned on a common axis that is parallel to the central axis A, as illustrated in FIG. 2A. In alternate embodiments, the plurality of spaced apart openings may not be aligned on a common axis but may be distributed along different linear axes of the wall of the sling catheter 160. For example, FIG. 2B illustrates an embodiment of a sling catheter 275 having openings 276 that are variably spaced and distributed along different linear axes of the sling catheter body. In other embodiments, it is contemplated that the sling catheter 160 may in fact have no pre-formed openings; but, rather, the anchor (which is delivered through the anchor delivery catheter), punctures through the sling catheter 160 and into tissue at locations decided upon by the physician during the procedure. In this case, the opening in the sling catheter 160 for the suture would be defined by the size of the suture(s).

FIG. 3 is a side view perspective of one embodiment of a steerable catheter that may be translatably disposed within the sling catheter 160 (FIG. 2A), or sling catheter 275 (FIG. 2B). For example, the steerable catheter may include an anchor delivery catheter 300 comprising a steerable shaft 310 extending from a distal end 305 to a proximal end 315. The proximal end 315 of the anchor delivery catheter 300 may include a handle 325 having a dial 330, or other control mechanisms that are configured to steer the distal end 305 of the catheter 300. For example, the steerable shaft 310 may comprise embedded pull cables which may be coupled to mechanisms in the handle 325 configured to deflect the distal end 305 of the catheter 300 as it travels through the lumens of arteries or veins into the left ventricle. It is appreciated that, although a dial 330 is shown, alternative steering control mechanisms may include, for example, thumbwheels, dials, knobs, switches, and the like and the disclosure is not limited by the manner of steering the anchor delivery catheter 300.

According to one aspect, the shaft 310 of the anchor delivery catheter 300 comprises a generally tubular structure having a lumen extending therethrough. The lumen has a diameter configured to enable translation of an anchor from the proximal end 315 to the distal end 305 of the catheter 300. In one embodiment, the distal end 305 of the anchor delivery catheter 300 includes one or more anchor ports, such as port 340. The port 340 is sized to allow an anchor to be expelled from the lumen of the anchor delivery catheter 300. In some embodiments, the diameter of the anchor port 340 relates to the diameter of openings of the associated sling catheter (e.g., such as openings 176 of the sling catheter 160 of FIG. 2A). In some embodiments, the diameter of the anchor port 340 is at least equal to the diameter of the openings in the associated sling catheter to facilitate passage of the anchor, although this is not a requirement.

In one embodiment, the anchor delivery catheter 300 may comprise a composite of layers of thermoplastic elastomer (TPE), for example PEBAX provided by ARKEMA corporation of Colombes, France. Alternatively, nylon, polyurethanes, polyester, silicone, or other similar materials may be used to provide thin walls that may be extruded and layered over braided wires or coils for tensile and hoop strength, although the disclosed system is not limited to any particular material composition for the anchor delivery catheter 300. In some embodiments, the length of the anchor delivery catheter 300 may range from between 24"-52", and more particularly between 42"-46". In one embodiment, the inner diameter may range between 0.25 mm to 11 mm. The outer diameter is related to the inner diameter of the sling catheter 160 and is sized to enable translation of the anchor delivery catheter 300 freely within the sling catheter 160. For example, the outer diameter may range between 0.75 mm to 11.5 mm In some embodiments, the handle 325 may comprise a coupler 350 configured to accept a push tube (such as push tube 355) or a guidewire, enabling the push tube 355 or guidewire to advance between the proximal end 315 and distal end 305 of the anchor delivery catheter 300.

Although the anchor delivery catheter 300 has been described as a steerable catheter, in alternate embodiments the anchor delivery catheter 300 may be a flexible catheter and steering of the sling catheter 160 into position may be achieved using a steerable guidewire.

FIG. 4 is a cross section of a distal end 405 of a delivery system 400 including a sling catheter 410 and an anchor delivery catheter 420 translatably disposed within the sling catheter 410. Delivery system 400, in various embodiments, may be formed similarly to delivery systems described above. The sling catheter 410 is shown to include a plurality of spaced apart openings 476. The anchor delivery catheter 420 is shown to include an anchor port 440. In one embodiment, the delivery system delivers anchors by aligning the port 440 of the anchor delivery catheter 420 with one of the openings 476 of the sling catheter 410. An anchor 450 may be advanced through a lumen of the anchor delivery catheter 420 towards the port 440, for example by a push tube 430 that is translatably disposed within the lumen of the anchor delivery catheter 420.

The anchor 450 may take a variety of forms. In some embodiments, the anchor 450 may be comprised of a shape memory material, for example a copper-aluminum-nickel, a nickel-titanium (NiTi) alloy, or other alloy of zinc, copper, gold and/or iron. In some embodiments the anchor 450 comprises a generally linear configuration facilitating translation through the lumen of the anchor delivery catheter 420 and biased towards an expanded configuration that inhibits translation of the anchor through the opening 476/port 440. For example, the anchor 450 is shown to include a talon 423a disposed at a distal end, and a suture coupler including an eyelet 423b disposed at the proximal end.

A suture 460 may be coupled to the anchor eyelet 423b. In some embodiments, the suture 460 may be tied to the eyelet 423b of the anchor 450, and in some embodiments the suture 460 may loop through the eyelet 423b, enabling cinching of anchors 450 as described in FIGS. 5A-5E.

The suture may be formed of any of a variety of biocompatible materials, including nylon, polyester, polymeric, or metallic wire or the like. In some embodiments, the suture may be braided and/or manufactured of two or more materials. Some other examples of materials (in addition to those noted) may include polypropylene, ultra-high molecular weight polyethylene, polyetheretherketone, polytetrafluoroethylene (PTFE), silk, or combination thereof. In some embodiments, the suture may be comprised of metals such as stainless steel and nitinol. For example, the suture may comprise a pre-shaped, heat-set Nitinol spring/braid/construction (i.e., Nitinol extension spring, spiral extensions, etc.) that are self-collapsing as it is deployed from the catheter around the papillary muscles, to bring the papillary muscles closer together.

FIGS. 5A-5E comprise top down views of a delivery system 500 that has been delivered into a left ventricle. In FIGS. 5A-5E, the sling catheter 510 and anchor delivery catheter 520 are shown in cross section. In some embodiments, the sling catheter 510 is looped around the papillary muscles PM1, PM2. In some embodiments, the sling catheter is looped around the base of the papillary muscles PM1, PM2. In alternate embodiments, the sling catheter 510 is positioned anywhere between the base of the papillary muscles PM1, PM2 and the mid-section of the papillary muscles PM1, PM2. It is appreciated that positioning the sling catheter 510 between the midpoint and base of the papillary muscles may reduce the potential that anchors interfere with the chordae tendinea.

Figure 5A:
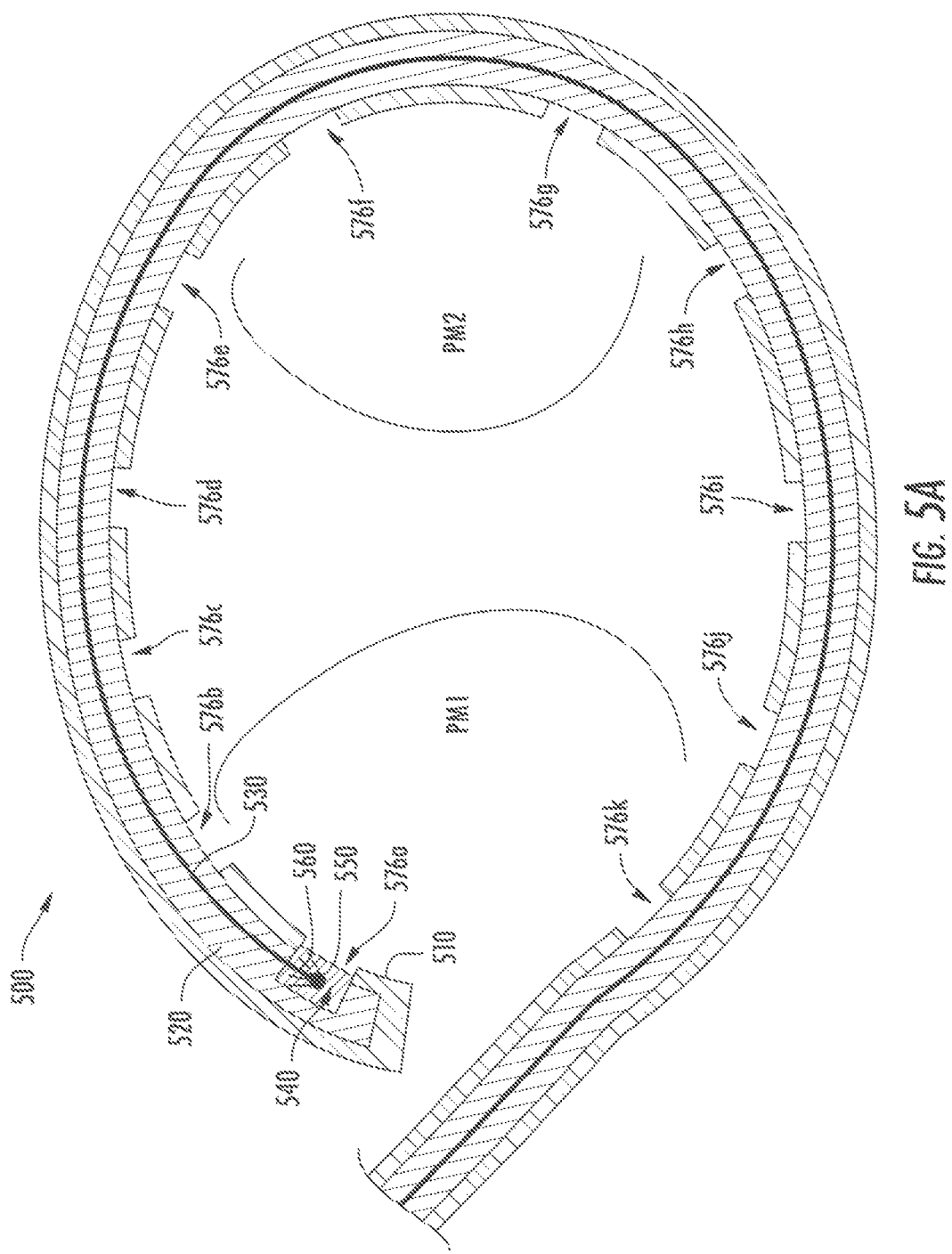

Once positioned, the sling catheter 510 may be contracted to engage an exterior surface, such an interior circumferential external surface, of the sling catheter with the papillary muscles PM1, PM 2. The sling catheter 510 may be advantageously positioned so that at least a portion of the openings 576a-576k are oriented towards the papillary muscles PM1, PM2, ensuring that anchors that are expelled from the delivery system 500 may affix to papillary tissue. FIG. 5A illustrates anchor 550 advanced to opening 576a by a push tube 530. The anchor 550 is coupled to a suture 560, which may be threaded over the push tube 530 back to the proximal end of the delivery system 550 (as shown in FIG. 4), or alternatively may be threaded through the push tube 530 as shown in FIG. 5A. In the embodiment of FIG. 5A, the anchor 550, which provides the first anchoring of the sling catheter 510, is shown tied to the anchor 550. The push tube 530 continues to advance, pushing the anchor 550 through the port 540 of the anchor delivery catheter and through the opening 576a to deploy the anchor 550 into tissue of the papillary muscle PM1.

Figure 5B:
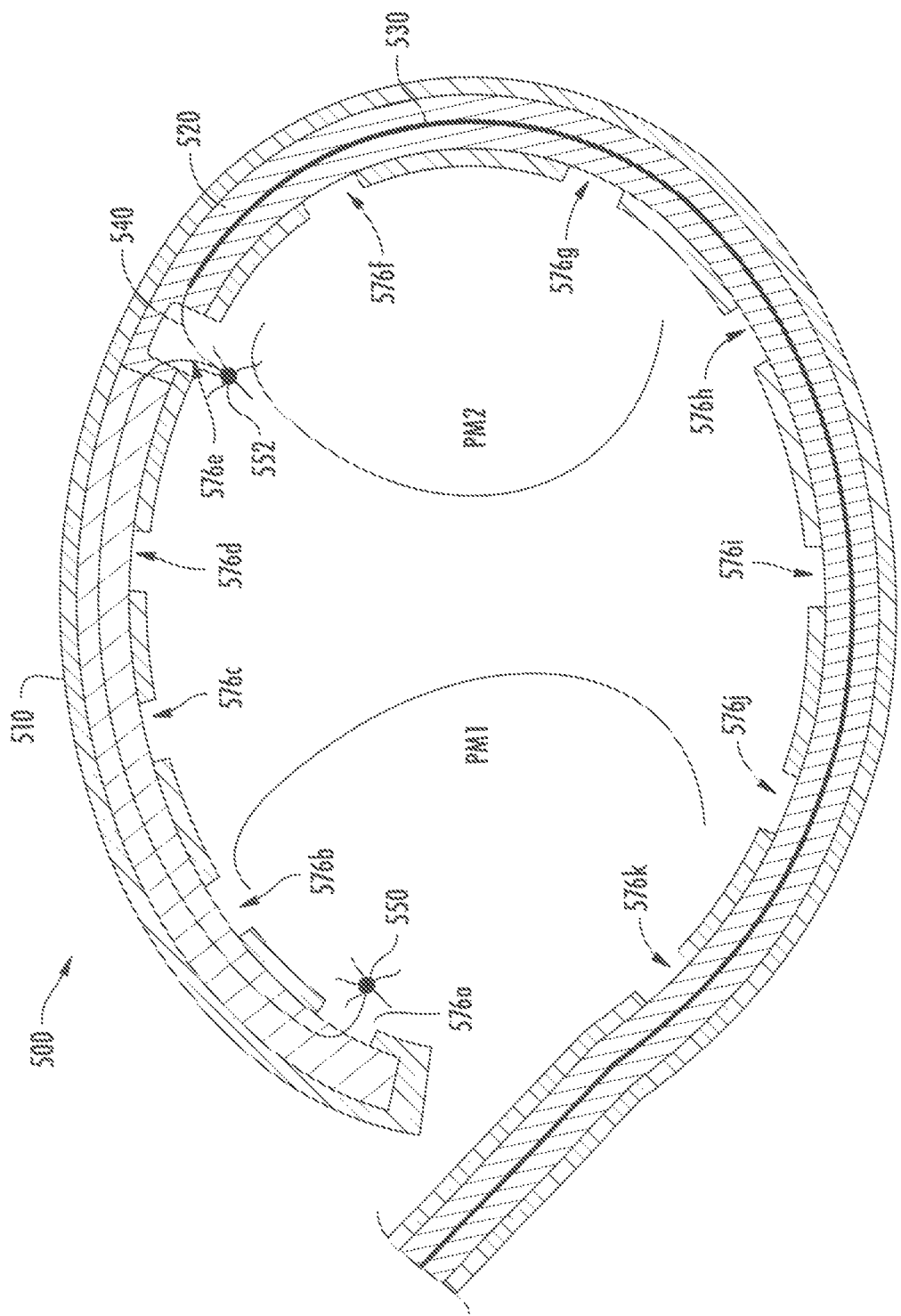

FIG. 5B illustrates deployment of a second anchor 552 by the delivery system 500. As shown, the first anchor 550 has been deployed and resumed its biased, expanded configuration which inhibits it being withdrawn back into the opening 576a of the sling catheter 510. A surgeon may choose any of the openings 576a-576k of the sling catheter 510 for deploying anchor 552, and FIG. 5B illustrates that anchor 552 is expelled through the port 540 of the anchor delivery catheter 520 and opening 576e of the sling catheter following proximal translation of the anchor delivery catheter 520 to align port 540 with opening 576e. Anchor 552 is then forwarded into papillary tissue PM2 by action of the push tube 530.

FIG. 5C illustrates the delivery system 500 following deployment of anchor 550 and anchor 552, each of which has returned to a biased configuration inhibiting return of the anchor into the respective openings 576a, 576e. In FIG. 5C, port 540 of anchor delivery catheter 520 has been proximally withdrawn to align port 540 with opening 576h of sling catheter 510, and push tube 530 is shown advancing anchor 554 to the port 540/opening 576h to deploy the anchor 554 into tissue of papillary muscle PM2. In FIG. 5D, it can be seen that delivery system 500 has deployed anchor 554 into tissue, the anchor delivery catheter 520 has been proximally withdrawn to align port 540 with opening 576k, and push tube 530 has advanced anchor 556 through the port 540 and opening 576k towards papillary tissue PM1. Suture 560 couples all four anchors 550, 552, 554, and 556, and the biased configuration of the anchors 550, 552, 554, and 556 inhibits their return into the sling catheter 510.

Figure 5E:
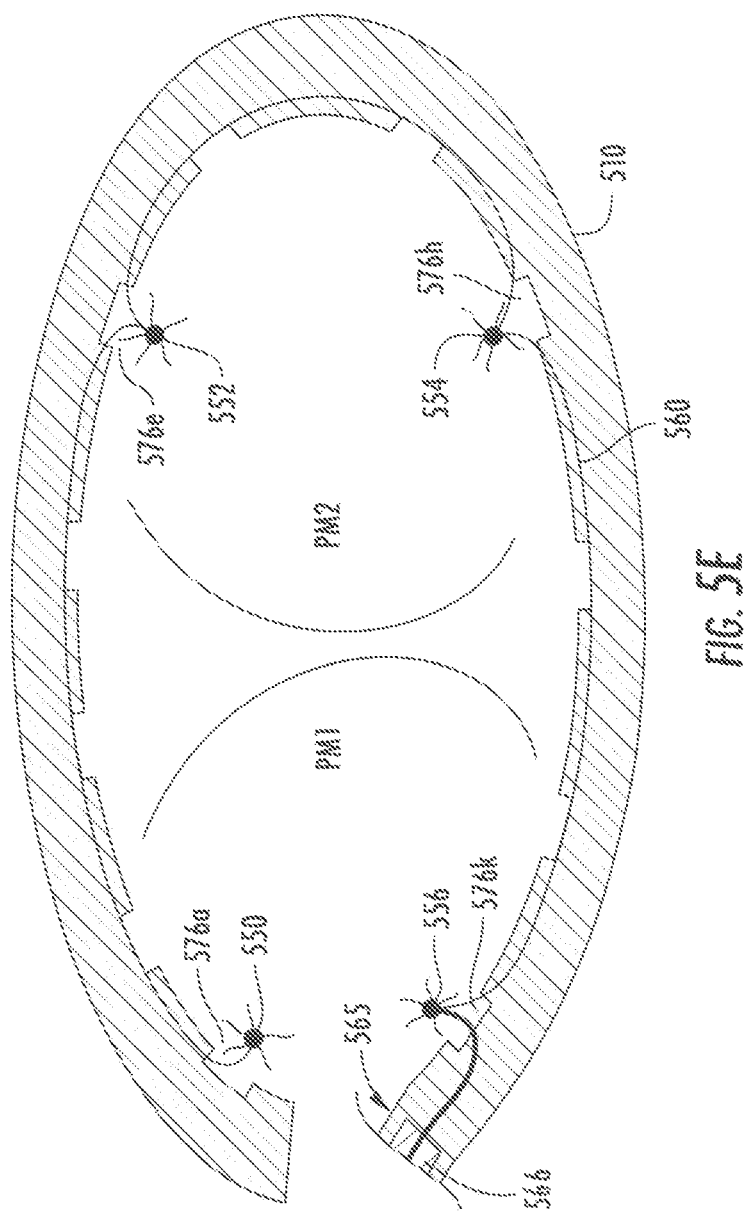

Accordingly, at this point the anchor delivery catheter may be withdrawn, and the proximal end of the suture 560 pulled proximally, or otherwise cinched, to draw the anchors, and the papillary muscles PM1, PM2 more closely together. For example, FIG. 5E illustrates sling catheter 510 following cinching of suture 560, wherein it can be seen that the papillary muscles PM1 and PM2 have been drawn together by the cinching action. Anchors 550, 552, 554, and 556, while drawn towards respective openings 576*a*, 576*e*, 576*h*, and 576*k* are inhibited from being drawn back into the sling catheter by their biased, expanded configuration. Once the suture 560 is tightened, the suture may be secured to the distal end of the sling catheter 510 to retain the cinched configuration of the sling catheter 510, for example using a resistive weld 565 or the like, the distal end of the sling catheter 510 may be detached at point 566, for example using cauterization or other means, and the remainder of the delivery system may be removed from the cardiac treatment site. Although FIGS. 5A-5E shows openings 576*a*, 576*e*, 576*h*, and 576*k* utilized for delivering respective anchors, it should be appreciated that more or fewer openings 576*a*-576*k* may be utilized to effectuate the desired change to the papillary muscles PM1, PM2.

Various methods of detaching the sling catheter may be employed. For example, an electrical current may be delivered to resistively heat a localized region of the catheter causing it to detach under a little tension or torsion. Such a sheath could include the electrical conductors within the wall of the removable portion of the sheath for this purpose. In other embodiments, the sling portion may be mechanically detached, e.g., using a push-rod that engages and causes it to "break away" from the removable portion, or a threaded joint may be provided between the sling catheter and the sling portion of the sling catheter, and the two portions may be detached by rotating the sling catheter to release the threaded portions. In still other embodiments, an energy source may be advanced through the lumen of the delivery catheter, such as a laser, to "cut" the two portions, leaving the sling behind.

It should be noted that although delivery of four anchors has been shown and described, sub-valvular improvement may be realized with as few as two anchors, or as many anchors as there are openings in the sling catheter, and/or, as many anchors that may be pushed through openings or walls of the sling catheter. Accordingly, the disclosure is not limited to the use of any particular number of anchors.

Figure 6A:
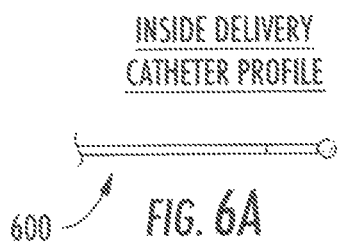
FIGS. 6A and 6B illustrate one embodiment of an anchor that may be used in embodiments disclosed herein.
Figure 6B:
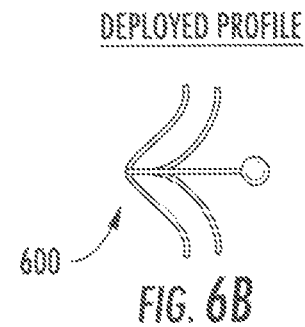
Figure 7A:
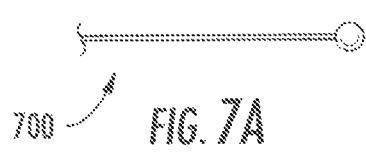
FIGS. 7A and 7B illustrate one embodiment of an anchor that may be used in embodiments disclosed herein.
Figure 7B:
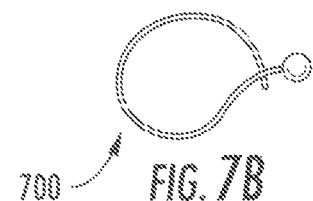
Figure 8A:
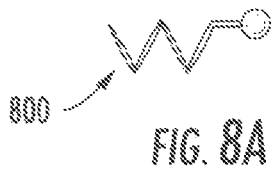
FIGS. 8A and 8B illustrate one embodiment of an anchor that may be used in embodiments disclosed herein.
Figure 8B:
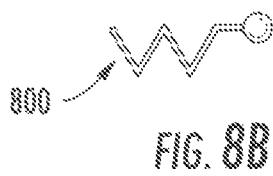

In addition, although the diagrams have shown an anchor with extended tines, the present invention is not limited to the use of a particular anchor, but rather may use any form of anchor that may travel freely within a lumen but inhibit return to the lumen following deployment. For example, FIGS. 6A-9B illustrate various embodiments of anchors that may be suitable for this purpose. FIG. 6A, for example, illustrates an anchor 600 in a linear configuration for translation within a lumen, and FIG. 6B illustrates the anchor 600 in an expanded configuration, wherein tines of the anchors extend radially outward. FIG. 7A illustrates a loop anchor 700 in a linear configuration and FIG. 7B illustrates the loop anchor in the expanded configuration. FIG. 8A illustrates a helical anchor 800 in a linear configuration and FIG. 8B illustrates the helical anchor as deployed, where the turns of the helical anchor would capture the edges of the port/openings to inhibit return of the anchor 800 into the sling catheter. The helical anchor may be incompressible (such that its diameter does not change when pushed through the catheter), for example, comprised of MP35N or stainless steel, or may be formed of a shape-memory material such as Nitinol that self-expands when released from the catheter.

Figure 9A:
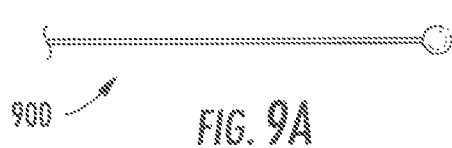
FIGS. 9A and 9B illustrate one embodiment of an anchor that may be used in embodiments disclosed herein.
Figure 9B:
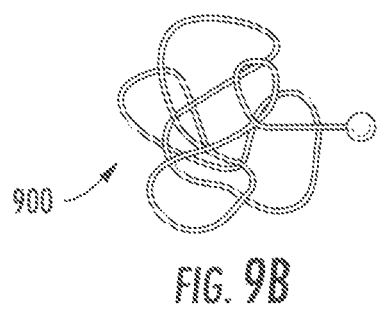

FIG. 9A illustrates a twisted anchor 900 in a linear configuration, and FIG. 9B illustrates the twisted anchor 900 in a deployed profile. The tine anchor 600, loop anchor 700 and twisted anchor 900 may each be formed of a memory-based material biased towards their expanded configurations, and/or may return to their biased configuration in response to body heat. In any of the various embodiments, the anchors may be comprised of stainless steel, nitinol, or the like, and may include a sharpened distal end and/or barbs disposed over portions of the anchor bodies to secure the anchor to a treatment site. The anchor may range from about 2 mm to about 15 mm in total axial length and from about 0.2 mm or less to 3 mm or more in diameter. However, other embodiments may be used depending upon the anchoring purpose, and thus the disclosure is not limited to a particular form of anchoring.

Figure 10:
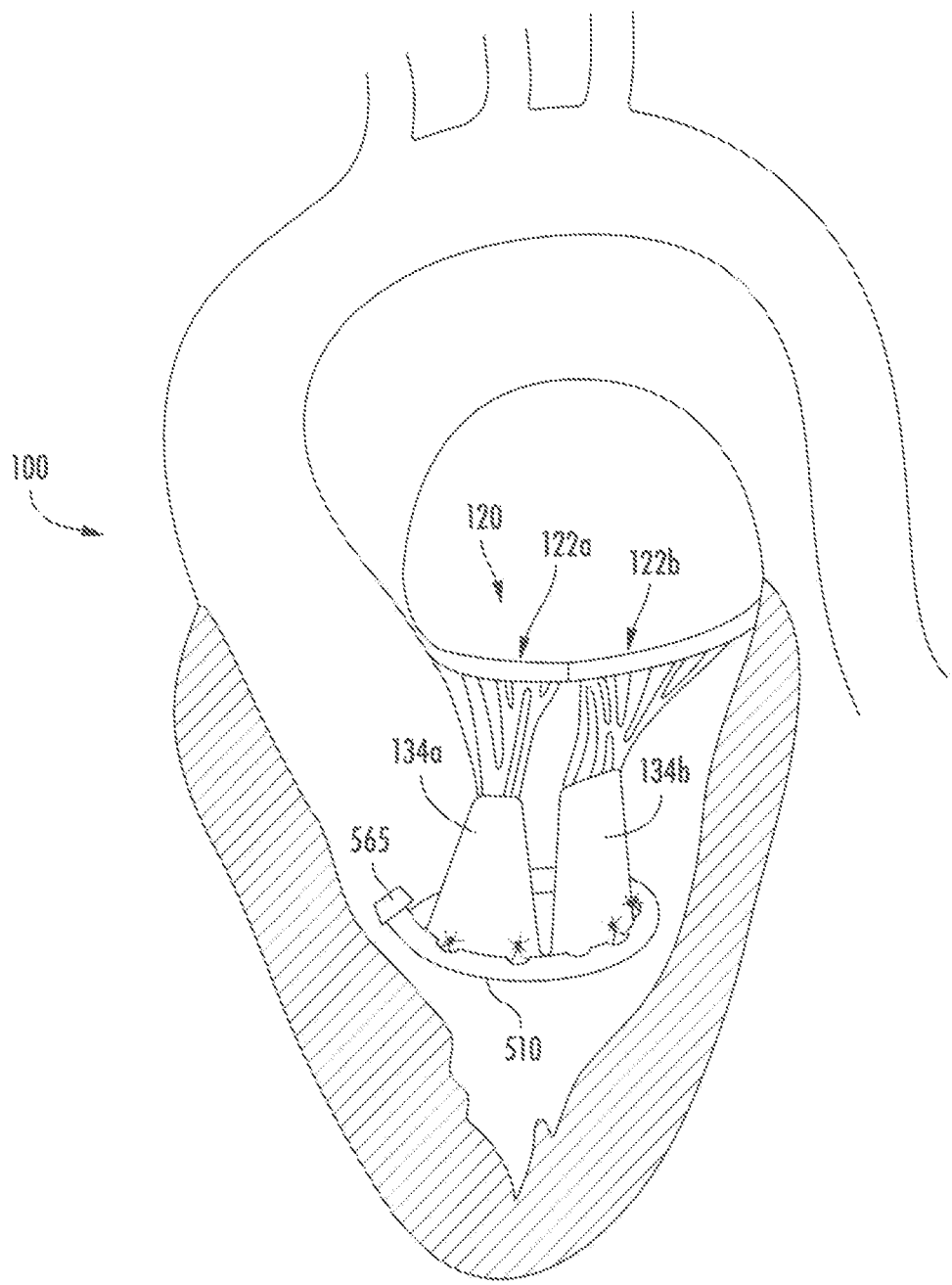
FIG. 10 is a diagram of a portion of a heart following sub-valvular repair as disclosed in one embodiment herein.

FIG. 10 is a diagram of the heart 100 of FIG. 1 following sub-valvular repair as disclosed in FIGS. 5A-5E. As shown in FIG. 10, the sling catheter 510 remains disposed about the papillary muscles 134*a*, 134*b*. The sling catheter 510 has been cinched using anchors and sutures and restrained in the cinched configuration by weld 565, holding the papillary muscles together and pulling together the leaflets 122*a*, 122*b* of the mitral valve 120 to restore cardiac function.

Accordingly, a system and method for sub-valvular repair has been shown and described. Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "example" is used exclusively herein to mean "serving as an example, instance, or illustration." Any implementation described herein as an "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination. Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The devices and/or methods disclosed and claimed herein can be made and executed without undue experimentation in light of the present disclosure. While various embodiments of the devices and methods of this disclosure have been described, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An implant comprising:
   a cinchable sling catheter having a first opening and a second opening, the first opening and second opening extending through a wall of the cinchable sling catheter;
   a first anchor configured to be disposed adjacent the first opening external to the sling catheter;
   a second anchor configured to be disposed adjacent to the second opening external to the cinchable sling catheter; and
   a cinchable suture carrying at least the first anchor and the second anchor, and configured to extend through a lumen of the cinchable sling catheter, and cinchable to cinch the cinchable sling catheter and to draw together the first anchor and the second anchor when the first anchor and the second anchor have been deployed with respect to tissue.

2. The implant of claim 1, wherein the first opening and the second opening are two of a plurality of spaced apart openings of the cinchable sling catheter, wherein the spaced apart openings are evenly spaced or variably spaced.

3. The implant of claim 1, wherein the cinchable sling catheter comprises a polytetrafluoroethylene tube.

4. The implant of claim 1, wherein the cinchable sling catheter is configured for circumferential disposal about one or more papillary muscles, and at least one of the first opening or the second opening is orientated towards the one or more papillary muscles when circumferentially disposed.

5. The implant of claim 1, wherein the first opening and the second opening are aligned along a common longitudinal axis of the cinchable sling catheter or are disposed along different longitudinal axes of the cinchable sling catheter.

6. The implant of claim 1, wherein the first anchor and the second anchor are two of a plurality of anchors of the implant, and wherein each anchor is biased towards a configuration that inhibits return of the anchor into the cinchable sling catheter.

7. A delivery system comprising:
   a first catheter having a proximal end, a distal end and a lumen extending from the proximal end to the distal end, a portion of the distal end of the first catheter comprising a cinchable sling having a plurality of spaced apart openings extending through a first catheter wall;
   a second catheter having a proximal end, a distal end, and a delivery lumen extending from the proximal end to the distal end, the distal end of the second catheter including a delivery port that extends through a second catheter wall, the second catheter translatably disposed within the lumen of the first catheter to enable alignment of the delivery port with one or more of the plurality of spaced apart openings of the cinchable sling;
   a plurality of anchors carried by a suture; and
   a push tube, translatably disposed within the delivery lumen and configured to advance at least one of the plurality of anchors through the delivery lumen and through the delivery port;
   wherein the suture is cinchable to cinch the cinchable sling and to draw together the anchors when the anchors have been deployed with respect to tissue.

8. The delivery system of claim 7, wherein the cinchable sling of the first catheter is formed of a polytetrafluoroethylene tube.

9. The delivery system of claim 7, wherein the cinchable sling of the first catheter has a higher flexibility than the second catheter.

10. The delivery system of claim 7, wherein an outer diameter of the cinchable sling is between 1 mm and 12 mm, a length of the cinchable sling is between 1 cm-35 cm and the plurality of spaced apart openings are spaced at least 2 mm apart.

11. The delivery system of claim 7, wherein the plurality of anchors are coupled via one or more sutures.

12. The delivery system of claim 11, further including a cinch mechanism configured to reduce spacing between the plurality of anchors.

13. The delivery system of claim 12, wherein the cinch mechanism is configured to detach the cinchable sling from the first catheter.

14. The delivery system of claim 12, wherein the cinch mechanism is configured to bind at least a portion of at least one of the one or more sutures to at least one of the plurality of anchors.

15. The delivery system of claim 7, wherein each of the plurality of anchors has a first configuration enabling translation through the second catheter and delivery port, and a second configuration that inhibits translation through the delivery port and wherein the second catheter retains the plurality of anchors in the second configuration.

16. The delivery system of claim 7, wherein the plurality of spaced apart openings of the cinchable sling are aligned along a common longitudinal axis of the first catheter or are disposed along different longitudinal axes of the first catheter.

17. The delivery system of claim 7, wherein the plurality of spaced apart openings are evenly spaced or a spacing of plurality of spaced apart openings varies.

18. The delivery system of claim 7, including a cinching mechanism for tightening the suture.

19. A method of sub valvular repair, the method comprising:
  advancing a catheter system to a left ventricle, the catheter system including a cinchable sling catheter having a plurality of openings extending through a distal wall of the sling catheter and a delivery catheter, translatably disposed within the cinchable sling catheter, the delivery catheter having a distal port extending through a wall of the delivery catheter;
  orienting the plurality of openings towards papillary muscles;
  advancing a first anchor, carried by a suture, towards the distal port of the delivery catheter, the first anchor having a linear configuration enabling translation of the first anchor through the delivery catheter;
  aligning the distal port with a first opening of the cinchable sling catheter and pushing the first anchor through the distal port and the first opening into first papillary tissue, the first anchor assuming a biased configuration that inhibits return of the first anchor into the first opening when the first anchor is pushed from the delivery catheter;
  advancing a second anchor, carried by the suture, towards the distal port of the delivery catheter, the second anchor comprising the linear configuration during translation through the delivery catheter;
  aligning the distal port with a second opening of the cinchable sling catheter and pushing the second anchor through the distal port and the second opening into second papillary tissue, the second anchor assuming the biased configuration that inhibits return of the second anchor into the second opening when the second anchor is pushed from the delivery catheter; and
  cinching the suture to cinch the cinchable sling catheter and to draw the first anchor and the second anchor together to adjust a spacing between the first papillary tissue and the second papillary tissue into which the first anchor and the second anchor have respectively been pushed.

20. The method of claim 19, further including:
  binding one or more portions of the suture to at least one anchor;
  detaching at least a portion of the cinchable sling catheter; and
  removing the catheter system from the left ventricle.

* * * * *